US006270644B1

(12) United States Patent
Mathies et al.

(10) Patent No.: US 6,270,644 B1
(45) Date of Patent: Aug. 7, 2001

(54) CAPILLARY ARRAY ELECTROPHORESIS SCANNER

(75) Inventors: Richard A. Mathies; James R. Scherer, both of Berkeley, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/238,131

(22) Filed: Jan. 27, 1999

(51) Int. Cl.[7] .................................................. G01N 27/26
(52) U.S. Cl. .......................... 204/603; 204/600; 204/601
(58) Field of Search ............................ 356/344; 204/451, 204/452, 601, 603; 422/70

(56) References Cited

U.S. PATENT DOCUMENTS

| | | | |
|---|---|---|---|
| 5,091,652 | 2/1992 | Mathies et al. ...................... | 250/458 |
| 5,354,538 | 10/1994 | Bunce et al. ......................... | 422/106 |
| 5,372,695 | 12/1994 | Demorest .............................. | 204/603 |
| 5,443,791 | 8/1995 | Cathcart et al. ...................... | 422/65 |
| 5,483,075 | 1/1996 | Smith et al. .......................... | 250/458 |
| 5,540,888 | 7/1996 | Bunce et al. ......................... | 422/100 |
| 5,560,811 | 10/1996 | Briggs et al. ........................ | 204/451 |
| 5,770,157 | 6/1998 | Cargill et al. ........................ | 422/99 |

OTHER PUBLICATIONS

Smith et al., 1986, 321 *Nature* 674–979 Jun.
Swerdlow, H. & Gestelord, R., 1990, 18 *Nuc. Acids Res.* 1415–1419 Month unknown.
Luckey et al., 1990, 18 *Nuc. Acids Res.* 4417–4421 Month unknown.
Cohen, A.S. et al., 1990, 516 *J. Chromato.* 49–60 Month unknown.
Mathies, R.A. & Huang, X.C., 1992, 357 *Nature*, 167–169, Sep.

*Primary Examiner*—Jill Warden
*Assistant Examiner*—Alex Noguerola
(74) *Attorney, Agent, or Firm*—Pillsbury Winthrop LLP

(57) ABSTRACT

A Monster Capillary Array Electrophoresis scanner measures four-color electropherograms from over a thousand capillary electrophoretic separations in parallel. The system consists of a two-dimensional confocal rotary scanner and a four-color detection unit.

21 Claims, 11 Drawing Sheets

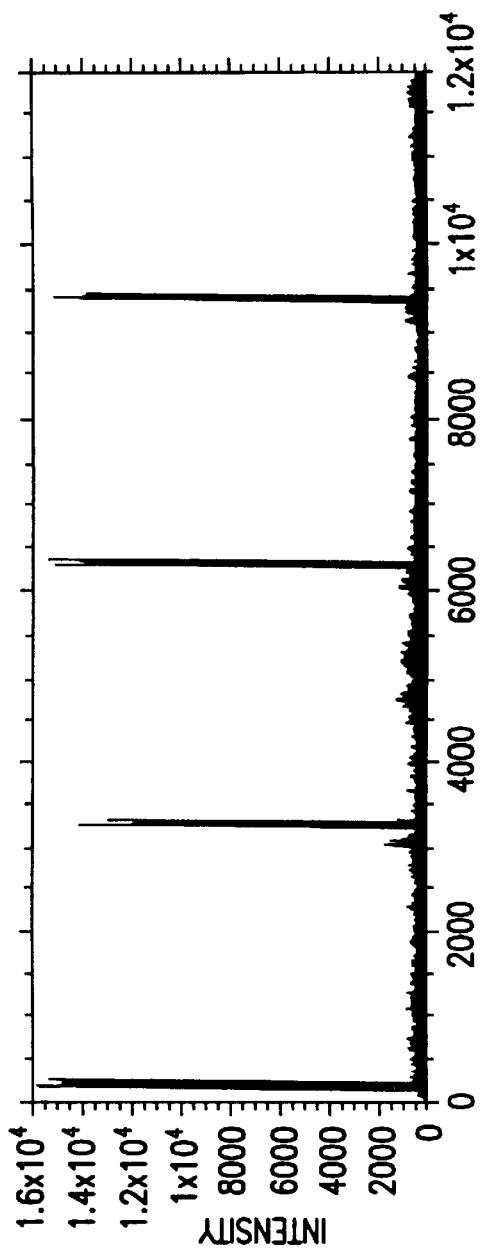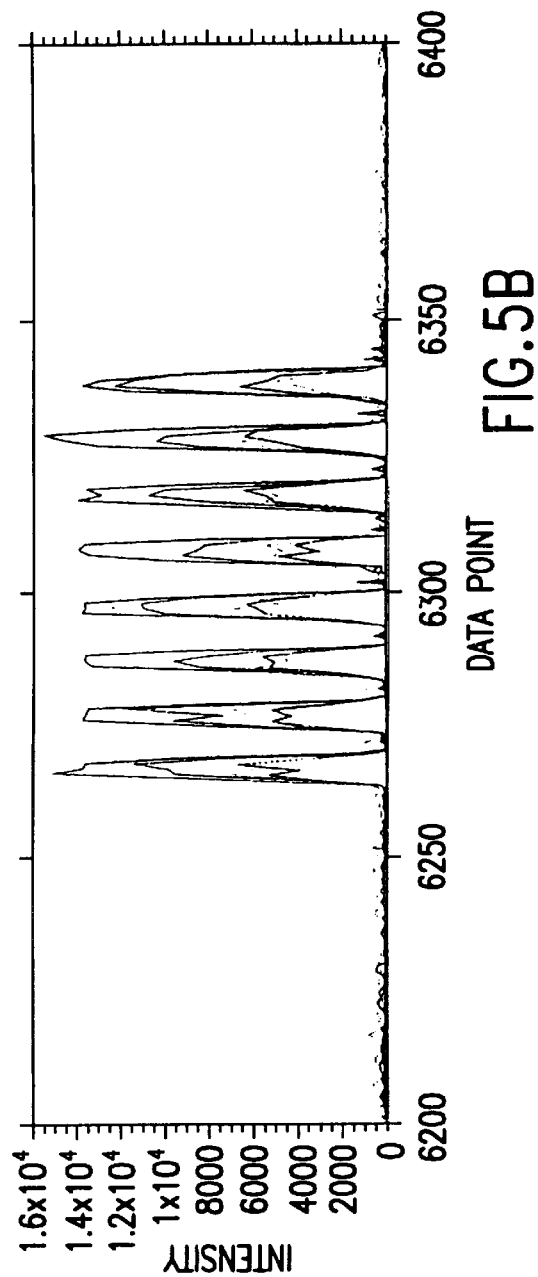

CAPILLARY ARRAY ELECTROPHORESIS SCANNER

BACKGROUND OF THE INVENTION

Research leading to portions of the present invention was funded in part through the National Institute of Standards and Technology ATP Grant to Affymetrix, Inc.

AREA OF THE ART

The present invention relates to methods and apparatus useful for facilitating the sizing of biomolecules with electrophoresis. In particular, the present invention relates to high volume analysis of aliquots of solutions especially useful in the context of systems for electrophoretic analysis, such as Capillary Array Electrophoresis ("CAE") of greater than 1000 capillary electrophoretic separations in parallel.

Analysis of Genomic DNA

An essential goal of biomedical research in the $21^{st}$ century will be the complete analysis of genomic DNA—the blueprint for life. This effort will involve not only the human genome—the genome of many organisms, both plant and animal, will be of profound importance to the human community. The ever-growing drive to determine the DNA sequence of complete genomes has created the need for the integration of automated instrumentation, bioinformatics, and sequencing chemistries into a high-capacity, high-accuracy process. Besides the human genome, the complete genomes of other animals, bacteria, fungi, and plants will be sequenced in the not-too-distant future. In the next decade, literally tens of billions of bases of novel DNA sequence will be acquired. Along with those novel sequences, confirmatory sequencing and mutant analysis projects for known genes will push further for increased capacity and reliability of sequencing sample preparation and reaction setup. Simplification and full automation of laboratory processes will have to provide the necessary increase in throughput and capacity, while guaranteeing reliability and reproducibility, if these goals are to be met.

As just one example of the wide-reaching importance of this work, the discovery of new medicines has been revolutionized by genomics. The human genome is believed to contain about 100,000 genes. The full human genome will be sequenced by 2003 resulting in an explosive increase in the number of drug targets, which currently number about 500. An estimated 3000–10,000 potential targets will be identified by 2003.

Another strategy is called positional cloning, in which genes associated with familial diseases are sequenced, have been used in an effort to identify new drug targets. For example, specific genes associated with diseases such as obesity or schizophrenia open the possibility of treating such conditions with drugs acting on specific targets.

Still a third strategy for identifying the specific genes responsible for regulating cellular processes such as differentiation and neoplasia has resulted in new targets for drug intervention. An elegant and conceptually simple procedure called Differential Display has revolutionized the approach to this scientific problem. The principle of this procedure is to represent each RNA "message" from a tissue on a gel, thereby creating an "RNA fingerprint" for each sample. The banding pattern obtained from, for example, healthy tissue, can then be compared with the banding pattern from cancerous tissue. Bands present in one sample, but not the other, represent genes expressed specifically in that tissue—in this case the cancerous tissue. The genes can then lead to the discovery of new targets for drug intervention.

All of these new analyses require high-throughput, high-capacity methods. In the past, access to genetic information has been limited by the low throughput techniques and instruments available for nucleic acid analysis. High throughput methods have the potential to dramatically change this situation, but even further improvements are needed. Thus, it is clear that the achievement of these important new goals is dependent on new types of biological instrumentation offering high-capacity, high-accuracy data acquisition coupled to computer tools for analyzing the resulting data.

Genes consist of four different chemical subunits, or bases-adenine (A), guanine (G), cytosine (C), and thymine (T)—attached to a sugar-phosphate backbone. The order of these bases, for example, GATTACA, determines the genetic message that leads to the production of particular proteins by the cell. Thus, we may compare the information contained in the sequence of A, G, C, and T in a gene as similar to the information contained in the sequence of the individual letters of the alphabet in a word. It is clear, therefore, that determining this sequence in a gene is crucially important to understanding the function of the gene.

Older methods for sequencing genes were developed around 1977–1980. They involved the use of specific chemical reactions on the genes, and the use of radioisotopes to identify the sequence of the different bases. An important separation step in the older methods involved the use of gel electrophoresis to sort gene fragments by size. In this method, a gel containing an appropriate buffer solution is cast as a thin slab between glass plates. Each end of the slab is electrified by the application of electrodes, to produce a positive end and a negative end of the slab. A small amount of the sample to be analyzed is pipetted onto the slab and the constituents of the sample are allowed to migrate along the slab under the influence of the electric field. The position of the different constituents of the sample on the gel is then determined by their molecular weight. A single slab can be divided into several lanes to make possible the analysis of several samples at the same time.

These older methods were effective, but slow and expensive. They made possible the sequencing of 3000–10,000 bases per person year, at a cost of $ 1–5 per base. However, there are billions of bases in the human genome alone, and it is clear that the development of faster, high-capacity, high-throughput automated methods would be of crucial importance to achieve the goal of sequencing entire genomes.

Automated DNA Analysis

In 1986, a method was developed at Cal Tech that used colored dyes as tags rather than radioactive isotopes for the four bases. Smith et al., 1986, 321 *Nature* 674–979. Each of the four colors-green, yellow-green, orange-red, and red—corresponds to a different base, so that it is possible to identify the different bases by means of their colored tags. Not only did this eliminate the need for radioactive isotopes, which pose problems in safe handling and disposal, but it also made possible the use of automated equipment in conducting the analysis.

A key to automating these methods was the development of capillary electrophoresis (CE), to replace the older gel slabs. In capillary electrophoresis, the gel is contained within a capillary tube rather than being layered as a slab on a glass plate. The capillary tube is a narrow-bore structure for performing high efficiency separations. High electric fields can be applied along the capillaries without significant temperature increases, and since the electrophoretic velocity of the charged species is proportional to the applied field, CE can achieve rapid, high-resolution separation. CE thus offers the advantages of nanoliter injection volumes, exceptional resolving power, fast separations in times ranging from a few minutes to less than one hour, less heat production, higher voltages, and reduced sample preparation. J.P., HANDBOOK OF CAPILLARY ELECTROPHORESIS, CRC Press, Boca Raton 1994.

In the automated system developed at Cal Tech, genetic material is chemically chopped into smaller segments wherein the terminal base in each segment is identified by a colored tag. All of the segments can then be separated by the process of electrophoresis, which sorts the segments according to their size as they pass through the gel. As the segments reach the end of the gel in the order of their size, they are illuminated by a laser, which causes them to fluoresce in their characteristic color. The fluorescence is then read out to identify the size and base terminus of the segment. Swerdlow, H. & Gestland, R., 1990, 18 *Nuc. Acids Res.* 1415–1419; Luckey at al. 1990 18 *Nuc. Acids Res.* 4417–4421; 1990, Cohen, A. S. et al. 516 *J. Chromato.* 49–60.

Although CE provides rapid analysis, total throughput is not high if only one capillary at a time is analyzed. This problem has led to the technique of running a number of capillaries in parallel. Mathies, R. A. & Huang, X. C., 1992, 357 *Nature*, 167–169. This approach uses an array of capillaries and is called capillary array electrophoresis (CAE). The combination of CAE and the non-radioactive colored tag methods opened the door to automating the sequencing of DNA. A commonly used automated DNA analysis system is the CEQ™ 2000 DNA Analysis System from Beckman Coulter (Fullerton, Calif.), which uses pre-assembled arrays of eight capillaries, thereby eliminating the need for laborious gel casting, plate washing and DNA sample loading. The eight capillaries are loaded by electro-kinetic injection of samples from the 8-well row of a 96-well, flat-bottom, polystyrene plate.

After the run is completed, a second eight well of a 96-well plate can be moved into position by an automated device, such as a Biomek® 2000 BioRobotics System (Beckman Coulter, Fullerton, Calif.). A second run can then be carried out using the eight capillary array, and the entire cycle can be repeated twelve times to complete the analysis of all of the 96 wells in the plate.

Although this type of automation is a distinct advance in developing high-throughput sequencing devices, still higher capacity is needed for the billions of analyses that must be carried out. Miniaturization of plate wells is a key to reaching the goal of carrying out large numbers of biotechnology analyses at a reasonable cost. To do this, the familiar 96-well plates are being displaced by 384-well plates (16× 24) in which the assay volumes are known to artisans, and the use of 1536-well plates (32×48 rows) is on the horizon. The advantages of these high-throughput devices include faster assays and significant cost savings.

What is now clear is that the current opportunities for automation involving 8-capillary arrays will not be adequate to address the large needs of DNA sequencing and that high-capacity, high-throughput instruments incorporating large numbers of capillary columns are required. Likewise, this is evinced by the ostensible commercial need for, and successes of, for example a 96 capillary array sequencer by the Molecular Dynamics Company of California.

CAE Confocal Fluorescence Scanning

Sensitive detection of fluorescently labeled analytes separated in small diameter capillaries is a difficult task. Because the capillaries have a diminutive diameter, a small focal volume is needed. The detection system must reject potentially strong Rayleigh scattering, fluorescence, and reflections from the capillary walls. R. A. Mathies, et al. (U.S. Pat. No. 5,274,224) disclose a laser-excited, confocal-fluorescence gel scanner in which the laser is focused on the sample by a microscope objective and the emitted fluorescence is gathered by the same objective using the applicable dimensions derived from this geometry followed by confocal detection. This has the advantage that the depth of a field of the optical system is sufficiently small that only the interior of the capillary is probed. Background scattering, stray fluorescence and reflections from capillary wall are rejected by spatial and spectroscopic filters. In, the '224 patent, the capillary array is moved to scan across the beam and detection system at a rate of 1 scan/second to image the migrating bands.

Rotary Scanning

As discussed further below, a rotary scanning apparatus for CAE has been described (D. H. Smith, et al., U.S. Pat. No. 5,483,075). The scanner of this apparatus provides relative motion in only one direction between an array of electrophoresis lanes and an optical detection system to collect data from each lane. However, this apparatus as taught is non-enabling for CAE systems of 100 tubes or greater in one of its two modes of relative motion for at least two reasons.

First, the detection zone is a discrete, very small area within each capillary. The zone is interrogated by a precisely focused beam of laser light. In the embodiments of the invention wherein the beam is held motionless and the array is moved, it is impossible to ensure that the beam will interrogate the precisely defined detection zone when 100 or more tubes are used. In moving arrays residing in holders of at least this size, complexity, and weight at the speed required to carry out 4 interrogations per second, it is impossible to insure the precise interrogation of the detection zone due to mechanical vibration introduced during movement of the array and its heavy holder. Hence, noise introduced into the data collection is sufficient to make the acquired data useless for its purpose and the embodiments of the invention wherein the beam is held motionless and the array is moved are non-enabling.

Second, it is possible to move small arrays, such as 8-tube arrays, alternately in both directions in a linear fashion. Under these circumstances the electrodes, running buffer containers, and associated wiring and tubing do not pose any special problems. However, in embodiments of large circular arrays where the array is moved in a single direction, the electrodes, running buffer, and all associated wiring and tubing would have to be moved with the array. Since the rotation speeds are usually about 4 rps to make it possible to adequately sample the detection zones, moving all of this equipment with the tubes would pose an insurmountable technical problem. Hence, all of these embodiments are non-enabling for large circular arrays.

Thus, there are substantial technical obstacles to the development of a scanning electrophoresis apparatus for high-capacity DNA sequencing. As pioneers and innovators attempt the development of a scanning electrophoresis apparatus for high-capacity DNA sequencing, none has approached it in combination with simplicity and reliability of operation, until the teachings of the present invention. It is respectfully submitted that other references merely define the state of the art or show the type of systems, which have been used to alternately address those issues ameliorated by the teachings of the present invention. Accordingly, further discussions of these references has been omitted at this time due to the fact that they are readily distinguishable from the instant teachings to one of skill in the art.

As discussed above, electrophoresis is a process by which the charged nature of significant biomolecular species and molecules can be used to sort them. Weak electrical fields are used to force DNA fragments, and the like, through a medium which separate them by offering different amounts of resistance to motion.

Prominent among the conventional methods and apparatus for the transfer of liquids are robotic and the like automated systems. However, owing to cost and the lack of flexibility of such systems numerous drawbacks have arisen. Likewise, the trend toward automating and enhancing the efficiency of DNA mapping and sequencing technology has pushed the envelope of several related fields of art which have been synthesized serendiptiously by the present inventors to generate the unexpected results of the present invention, by which over a thousand capillary electrophoretic solutions have been transferred in parallel. Various U.S. Letters Patent define the state of the art.

By way of further background, the utility of, and means for the detection of samples within capillary tubes using methods such as confocal microscopy are addressed by U.S. Pat. No. 5,091,652 ("Mathies et al.") which issued on Feb. 25, 1992.

U.S. Pat. No. 5,443,791 ("Cathcart et al."); issued Aug. 22, 1995 and assigned to the Applied Biosystems Division of Perkin Elmer disclosed an Automated Molecular Biology Laboratory. The high cost and complexity of the robotic translation mechanism of this device differentiates the same from the teachings of the present invention.

Likewise, U.S. Pat. No. 5,770,157 ("Cargill et al."); issued Jun. 23, 1998 to the Ontogen Corporation for Methods and Apparatus for the Generation of Chemical Libraries focused upon the costly and time intensive facilitation of robotic manipulation. Users of these kinds of systems continue to demand more flexibility and more cost efficiency, as demonstrated by the present invention.

U.S. Pat. No. 5,540,888 ("Bunce et al."); issued Jul. 30, 1996 to the British Technology Group, Ltd., for Liquid Transfer Assay Devices is further representative of the state of the art. However, the Bunce et al. device requires first, second, third and fourth flow channels of porous material, in contradistinction to the present invention.

Application Specific Capillary Electrophoresis was disclosed by U.S. Pat. No. 5,372,695 ("Demorest"); held by Applied Biosystems, Inc., which issued on Dec. 13, 1994. This system addressed the need for application specific flexibility, but included a complex serving apparatus which impeded its commercialization. According to the present invention, any number of capillaries may be handled, and no need for the expensive serving apparatus required by Demorest arises owing to the speed and industrial efficiency inherent in the teachings of the present invention.

Alternately, disposable one-time use devices are known, such as that disclosed in U.S. Pat. No. 5,354,538 ("Bunce et al."); issued Oct. 11, 1994. Nothing in the disclosure indicates that it can keep pace with known CAE Electrophoresis systems, as is a prime object of the present invention.

U.S. Pat. No. 5,560,811 ("Briggs et al.") issued Oct. 1, 1996 and is assigned to Seurat Analytical Systems, Inc. The subject matter is a method and apparatus for multiplexing electrophoresis analysis. Briggs et al. offers for consideration an excellent summary of the evolution of the instant technology and a thorough description of the state of the art.

Finally, as discussed above at the beginning of this section, U.S. Pat. No. 5,483,075 ("Smith et al.") which issued Jan. 9, 1996 and is assigned to the Perkin-Elmer Corporation, appears to be related to the teachings of the present invention. However, there is no teaching respecting the use of applicant's multiplicity of tubes being held stationary while an excitation beam and detection means sweep, as is demonstrated according to the present invention. Likewise, Smith stresses 'relative' motion between the beam and the tubes which includes moving either the beam, moving the tubes, or doing both. To try to move so many tubes at 1–10 rps generates so much vibration that it becomes difficult to accurately excite or detect defined regions within the tubes. Thus, the Smith reference teaches away even though the actual description and the drawings imply that the beam moves and the tube is stationary. Likewise, although rotary, Smith is not necessarily confocal, which generates major performance differences.

It is respectfully submitted that each of the discussed references merely defines the state of the art, or highlights the problems addressed and ameliorated according to the teachings of the present invention. Accordingly, further discussions of these references is omitted at this time due to the fact that each of the same is readily distinguishable from the instant teachings to one having a modicum of skill in the art, as shall be demonstrated by the claims which are appended hereto.

OBJECTS AND SUMMARY OF THE INVENTION

According to a feature of the present invention, there is provided, in one general embodiment, an arrangement by which the capillary tubes are mounted on the sides of two externally connected cylinders connected through bearings to the rotor means. The tubes may be mounted in grooves on the sides of said cylinders, wherein said cylinders are externally connected by at least three rigidly attached posts. In another embodiment, the tubes are substantially adjacent. The device may incorporate at least about 1024 tubes, wherein the tubes have an internal diameter up to those ranges which artisans would understand are appropriate with the present invention.

According to another general embodiment, computer means for process control, data processing, and for controlling the rotor, are provided.

In still another general embodiment, the rotor means is connected to a micro-stepping indexed motor.

In yet another general embodiment, the detector means is a four-color detection means incorporating photomultiplier means.

In yet still another general embodiment, the first radiant energy at about 488 nm is passed through a calibrated quarter-wave.

In a yet still additional and further general embodiment, the first radiant energy is disposed to initiate data acquisition by the detector means by illuminating a photodiode situated ahead of the tubes.

In again a yet still further general embodiment, the source of the first radiant energy is a coherent light source, which may be a laser. The detector means may be a two-dimensional image array detector/selected from a group consisting of a charge-coupled device (CCD) and a charge-injection device (CID) or a photomultiplier or a photo diode.

According to another aspect, there is provided an improved apparatus for determining the base sequence of a nucleic acid sample, wherein the components of the nucleic acid sample are labeled with one of four fluorescent dyes which fluoresce at four different wavelengths, each dye being attached to fragments terminating at a different one of A, G, C, or T bases, is provided, wherein the improvement comprises a high-capacity capillary array electrophoresis apparatus comprising at least 100 elongated cylindrical capillary tubes disposed in a circular array, a source of a first radiant energy of a first wavelength, an objective lens for receiving and focusing said radiant energy in an excitation volume in any one appropriately located said tube, a rotor means for rotating in a single direction, said rotor means containing a reflector and said lens for moving and positioning said reflector and said lens while keeping said tubes in a fixed position, whereby said excitation volume sequentially and repetitively is within one of said tubes, whereby material within said excitation volume is raised to an excited state, whereby said material is caused to generate a second radiant energy of a second wavelength, said objective lens serving to collect said second radiant energy and for directing said second radiant energy to confocal spatial and spectral filter means for transmitting said second radiant energy of a second wavelength and rejecting radiant energy of other wavelengths, and a detector means for measuring the intensity of said second radiant energy.

The foregoing and other objects of the invention are achieved by a high-capacity capillary array electrophoresis apparatus comprising in one aspect at least 100 elongated cylindrical capillary tubes disposed in a circular array, a source of a first radiant energy of a first wavelength, an objective lens for receiving and focusing said radiant energy in an excitation volume in any one appropriately located said tube, and a rotor means for rotating in a single direction. The rotor means contains a reflector and said lens for moving and positioning the reflector and lens while keeping the tubes in a fixed position, whereby the excitation volume sequentially and repetitively is within one of the tubes. Thus the material within the excitation volume is raised to an excited state, whereby the material is caused to generate a second radiant energy of a second wavelength, the objective lens serving to collect the second radiant energy and for directing the second radiant energy to confocal spatial and spectral filters for transmitting the second radiant energy of a second wavelength, and rejecting radiant energy of other wavelengths. A detector means for measuring the intensity of the second radiant energy is also provided.

These and other objects are accomplished by the parts, constructions, arrangements, combinations and subcombinations comprising the present invention, the nature of which is set forth in the following general statement, and preferred embodiments of which—illustrative of the best modes in which applicant has contemplated applying the principles—are set forth in the following description and illustrated in the accompanying drawings, and are particularly and distinctly pointed out and set forth in the appended claims forming a part hereof.

DESCRIPTION OF THE FIGURES

The file of this application contains at least one drawing executed in color. Copies of this patent with color drawings will be provided by the Patent and Trademark Office upon request and payment of the necessary fee.

The above-mentioned and other features of this invention and the manner of obtaining them will become more apparent, taken in conjunction with the accompanying drawings. These drawings depict only a typical embodiment of the invention and do not therefore limit its scope. They serve to add specificity and detail, in which.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, the abbreviations for any protective groups, amino acids, and other compounds, are, unless indicated otherwise, in accord with their common usage, or recognized abbreviations.

The following examples demonstrate the accuracy and usefulness of the invention in terms of the positional accuracy of the scanner (Example 1) and the high quality of 128 capillary sequencing runs (Example 2). The examples also demonstrate usefulness of the invention in DNA sequencing. These examples are illustrative, but not limiting, of the method and apparatus of the present invention. Other suitable modifications and adaptations of the variety of conditions and parameters normally encountered in DNA scanning procedures or which are obvious to those skilled in the art are within the spirit and scope of the invention.

EXAMPLE 1

Positional Accuracy of the Scanner Using 33 Capillaries

Figure 5C:
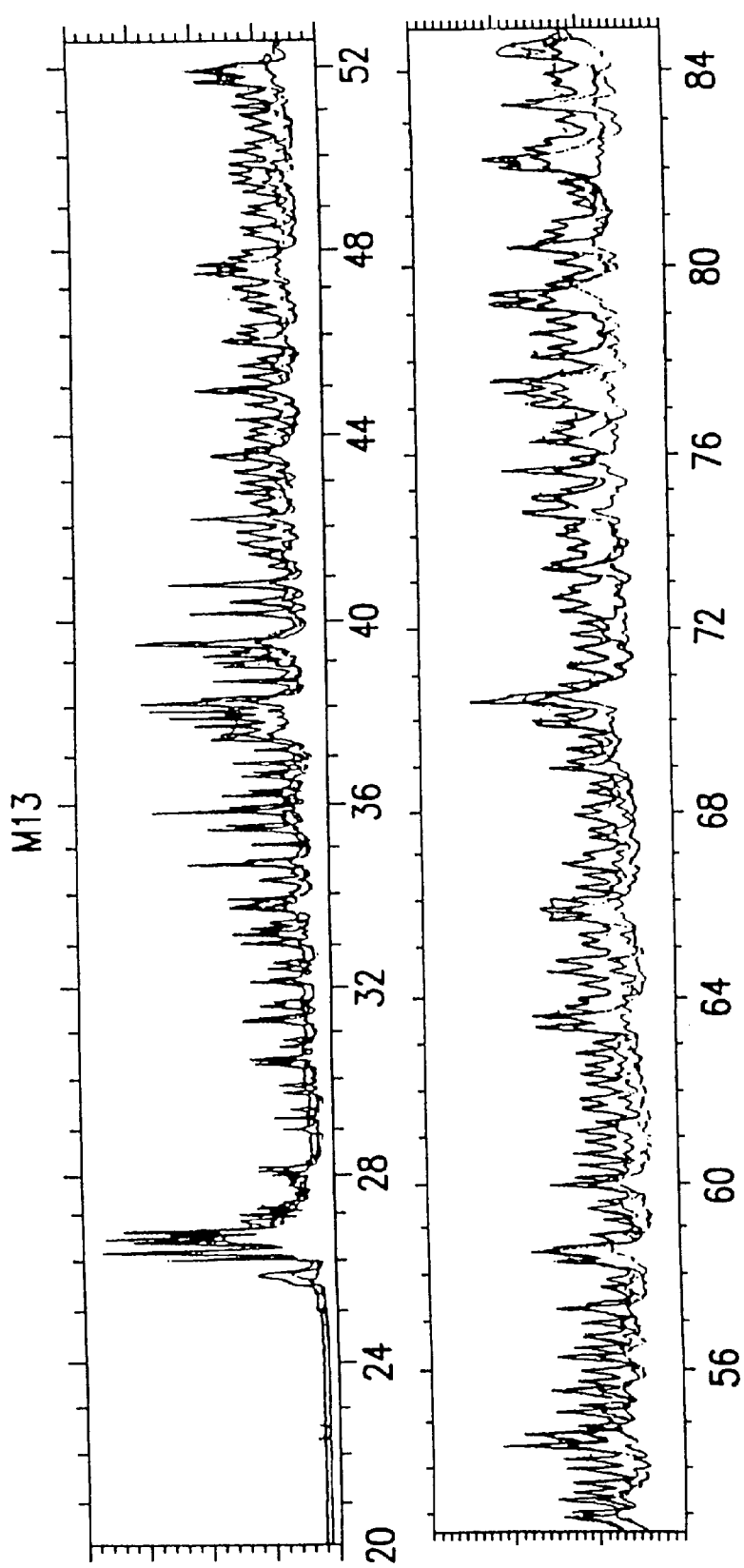
FIG. 5 shows a series of optical tests of the MCAE scanner, including:
(A) This trace displays fluorescence data recorded from four groups of eight capillaries one in each quadrant of the scanner head,
(B) This trace presents a blow up of the data from A showing the resolved optical image of each capillary,
(C) Four-color M13 sequencing trace recorded from one capillary in the MCAE scanner using standard sample preparation and loading methods for capillary sequencing; and, FIG. 6 is an Image of M13 DNA sequencing traces performed on a 128 capillary array in the MCAE system.

Groups of eight capillaries were arranged at the beginning of each of the four quadrants of the scanner and one capillary at the end of the last quadrant. A 1 nM fluorescein solution in 1×TBE was circulated through the resulting 33 capillaries and the fluorescence signals were detected from 1 rotation of the scanner (21,500 points). FIG. 5A shows a trace that displays fluorescence data recorded from four groups of eight capillaries, one in each quadrant of the scanner head. The laser power was 240 mW at the sample. The blue, green, black and red traces are the signals from channels 1–4 (520 nm, 550 nm, 580 nm, >600 nm). FIG. 5B shows the group of eight capillaries in the third quadrant representing a blow-up of the data from FIG. 5A showing the resolved optical image of each capillary. FIG. 5C presents the results of a sequencing run of M13 in one capillary under scanning conditions. FIG. 5C is a four-color M13 sequencing trace recorded from one capillary in the high capacity scanner of the present invention using standard sample preparation and loading methods for capillary sequencing. The S/N of this run is as good or better than conventional flat bed capillary array scanners.

EXAMPLE 2

Positional Accuracy of the Scanner Using 33 Capillaries

Using the equipment and conditions employed in Example 1, a similar run was made using 33 capillaries. Similar data was obtained.

EXAMPLE 3

128-Capillary Sequencing Runs

Figure 6:
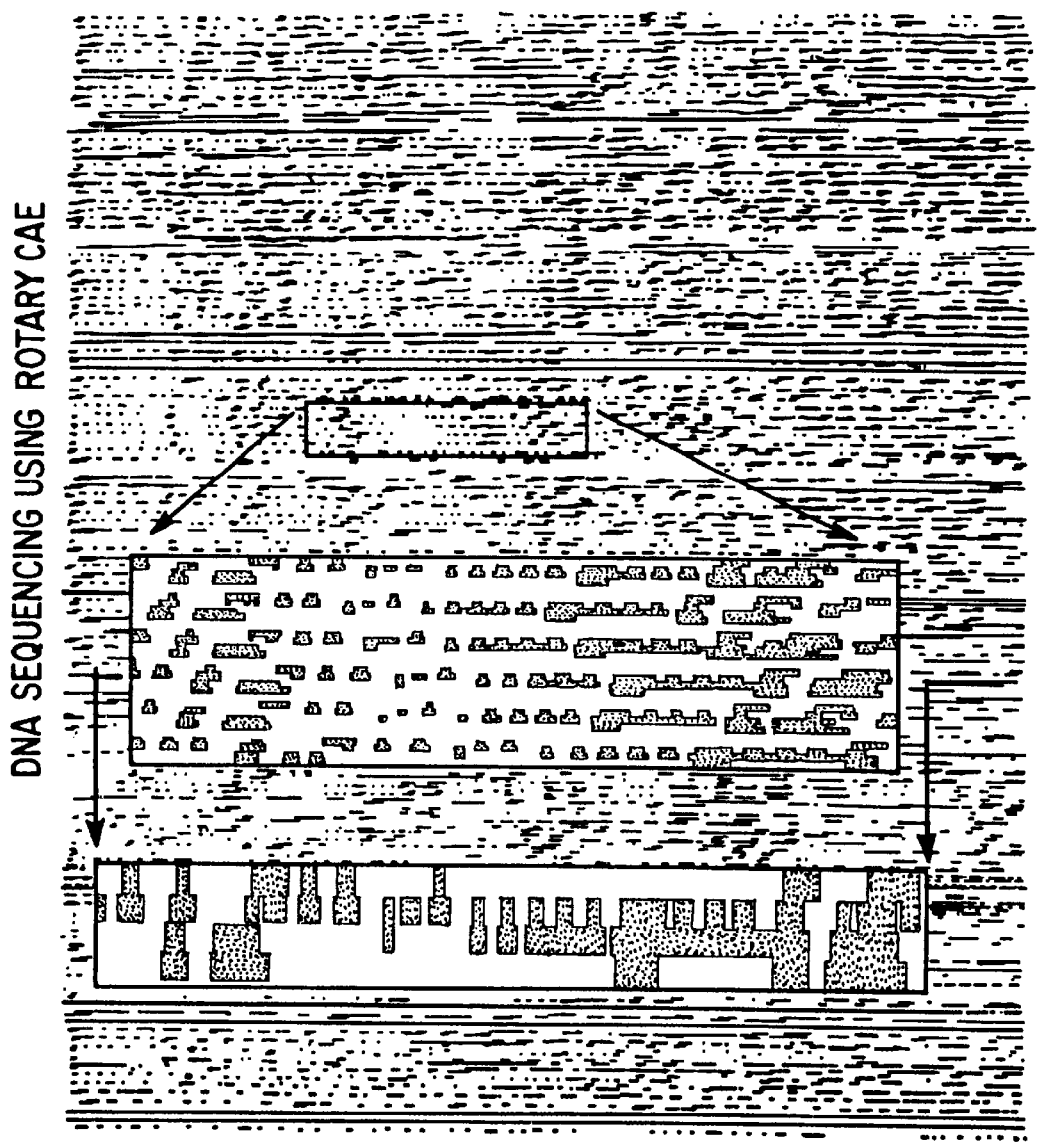

The results of 128-capillary sequencing runs detected with the high-capacity scanner of the present invention are shown in FIG. 6. FIG. 6 is an image of M13 DNA sequencing traces performed on the 128-capillary array. This image shows that high quality sequencing runs can be readily obtained on large numbers of capillaries in parallel. Each of these separations can be called to over 500 bases.

The Monster Capillary Array Electrophoresis scanner, shown generally at 100, was designed to measure four-color electropherograms from over a thousand capillary electrophoretic separations in parallel. The system consists of a two-dimensional confocal rotary scanner 300 and a four-color detection unit 200.

Figure 2A:
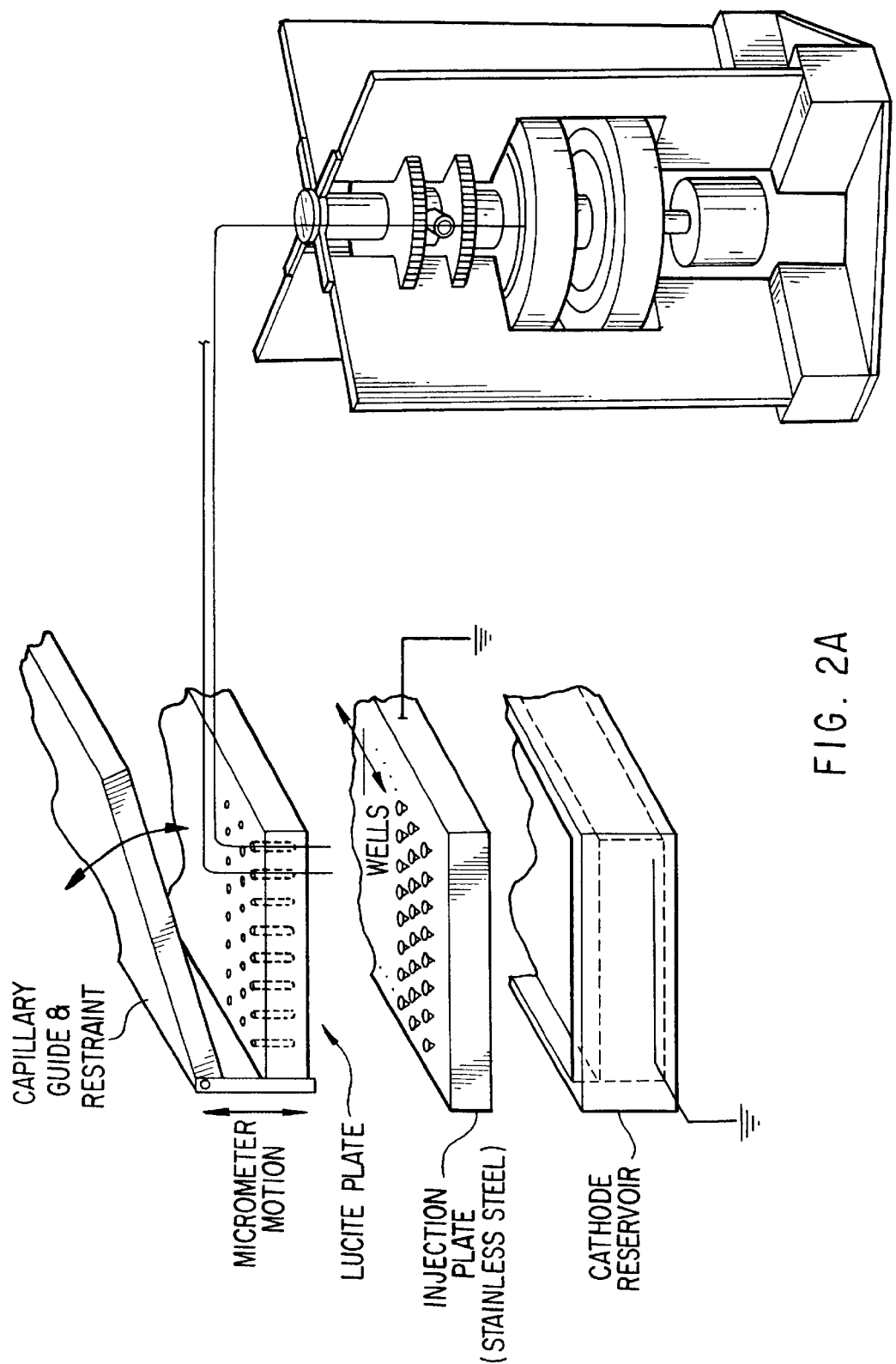
FIGS. 2A–C show a prototype Capillary Array Eklectrophoresis (CAE) scanner.
Figure 2B:
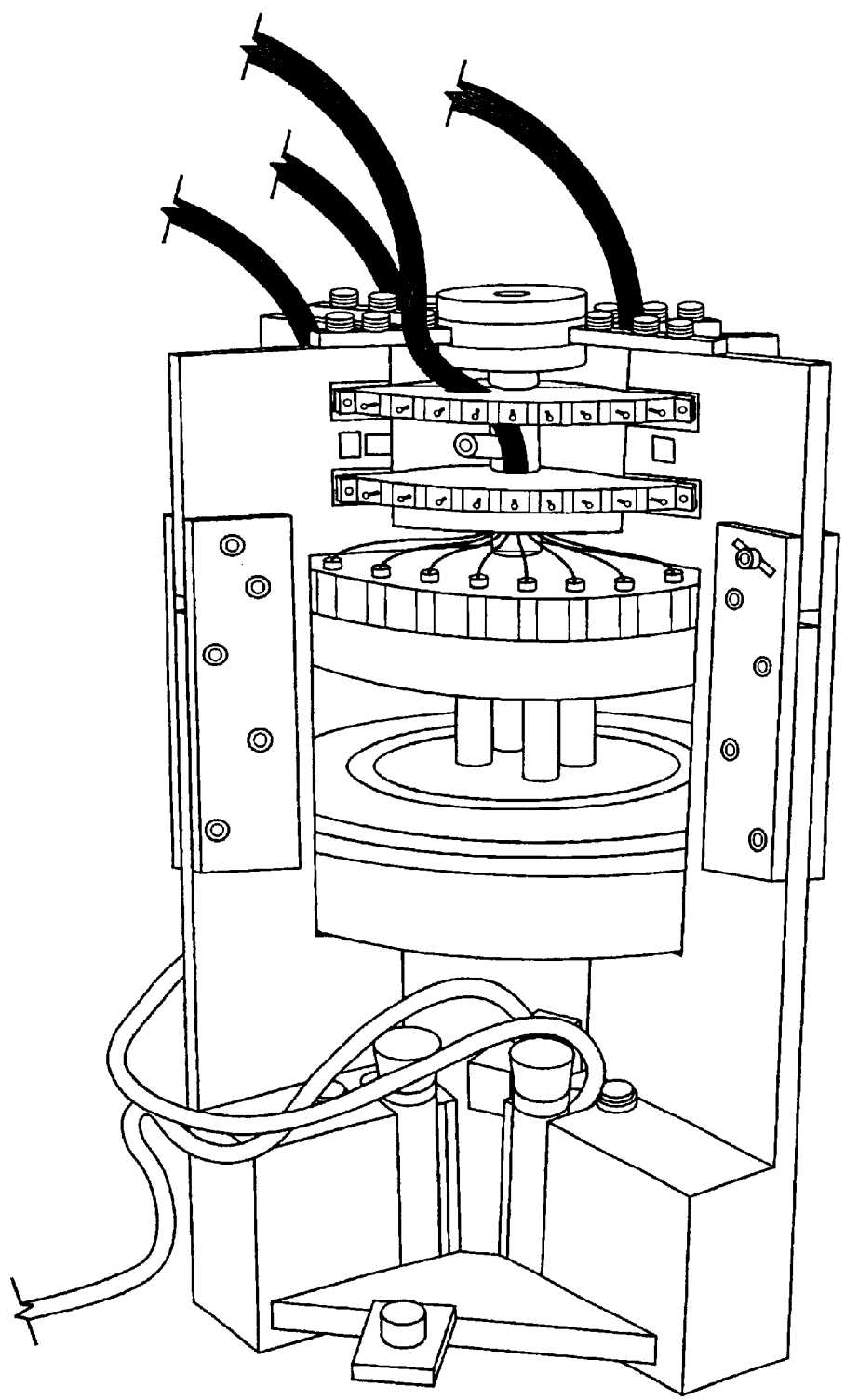
Figure 2C:
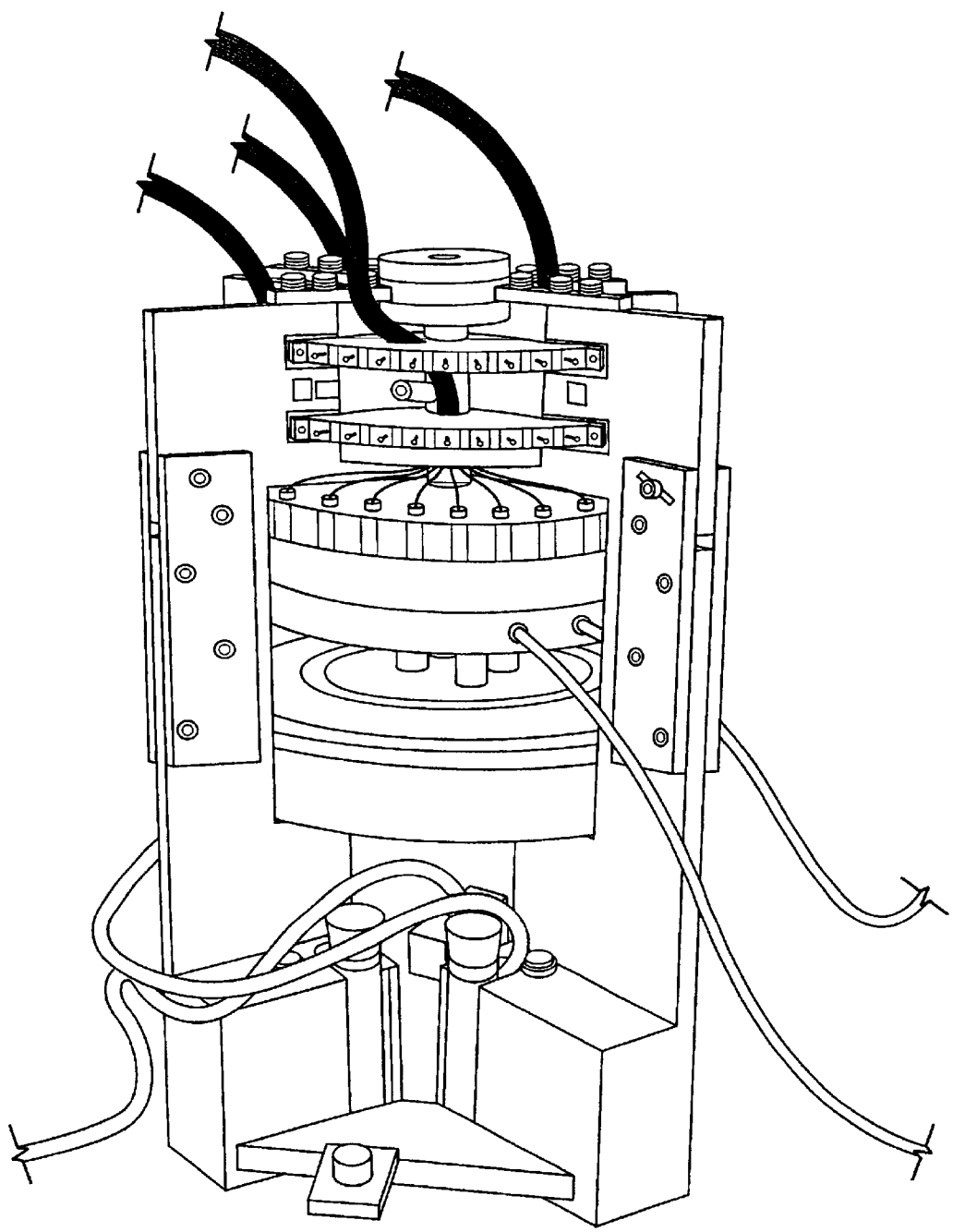
Figure 2D:
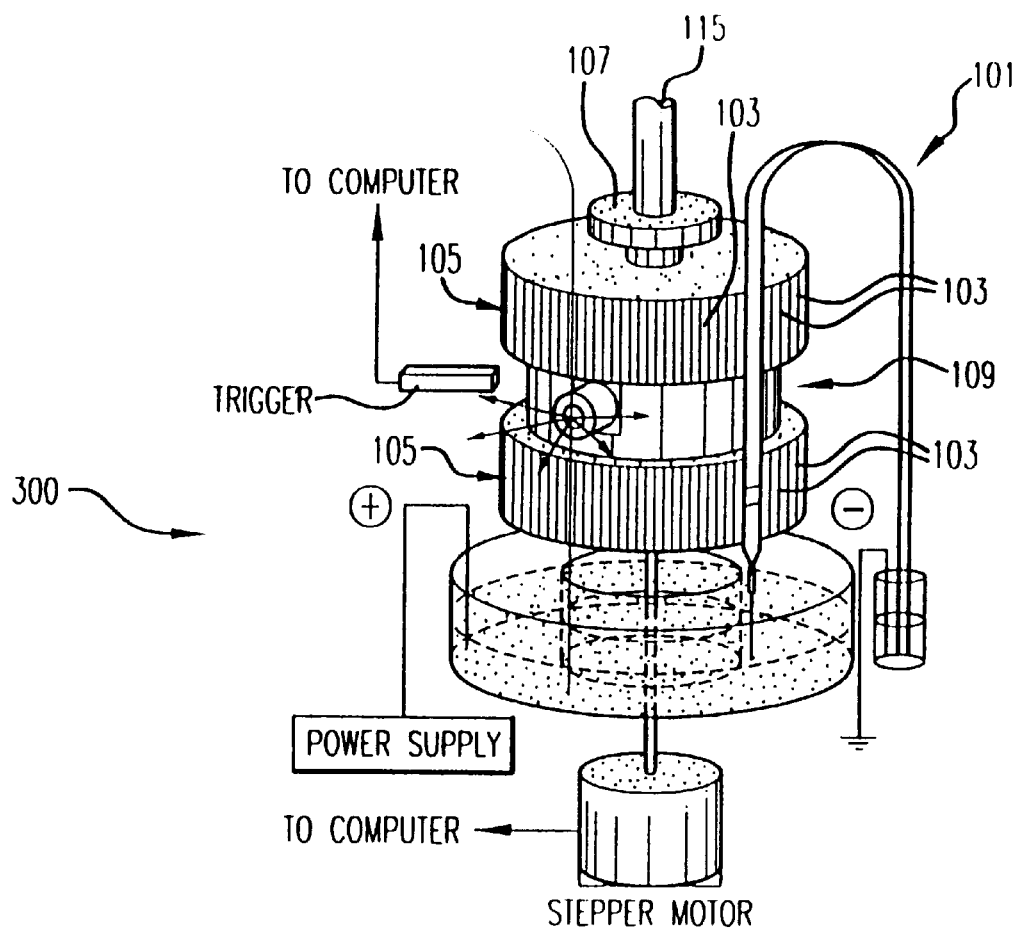
FIG. 2D shows the confocal rotary scan head for the CAE system bottom.

Referring now to FIG. 2D, a schematic diagram of the rotary scanner is offered for consideration. According to a preferred embodiment illustrated herein, for example, two hundred micron diameter capillaries 101 are mounted in machined grooves 103 (0.005" depth with a repeat spacing of 260 microns) on the sides of two externally connected cylinders 105, which may be constructed to be roughly four inches in diameter according to this embodiment.

Cylinders 105 are connected through two precision bearings 107 to a central rotor assembly 109 containing a diagonal mirror 111 and a microscope objective 113 that can be focused on the capillaries 101. The shaft 115 through the upper cylinder 105 is hollow to allow passage of the laser beam to the diagonal mirror 111 and the objective 113.

The rotor shaft below the diagonal mirror is solid and is connected to a micro-stepping indexed motor (not shown) through a flexible coupling.

The instrument is shown in FIGS. 2A–C. The cylinders that hold the capillaries are rigidly attached to four outside posts that divide the capillaries into four quadrants. Rings that span each quadrant are attached to the outside posts which support 32 fasteners, each of which can hold 32 capillaries in their respective places on the grooved cylinder. Capillaries are prepared in pre-spaced bundles of 32 and can be pressure filled with separation matrix in situ.

A group of 32 capillaries are brought together through a stainless steel sleeve, which fits into a two piece Lucite pressure adapter assembly (FIG. 2a). The capillaries are sealed inside the stainless steel sleeve with epoxy cement and the individual sleeves are pressure sealed with modified HPLC fittings. The capillaries are force filled with replaceable matrix (HEC or linear acrylamide) by positioning the open ends at the bottom of a trough in the lower plate containing the matrix and applying pressure with He gas. The upper and lower Lucite plates are bolted together and the trough is sealed between two concentric O-rings. The unit has been pressure tested to withstand 1000 psi. After filling the capillaries with matrix, the lower pressure chamber is unbolted and lowered and the two half wells containing running buffer and electrodes (lower part of FIG. 2b) are bolted to the upper adapter plate (FIG. 2c). Our electrophoretic separations are carried out with fields of 100–125 V/cm and the total current in this system can exceed 10 mA. To provide adequate safety, we use two power supplies individually fused at 6 mA and two independent running buffer anode wells. The running buffers in both the anode and cathode reservoirs can be recirculated with peristaltic pumps.

Figure 3:
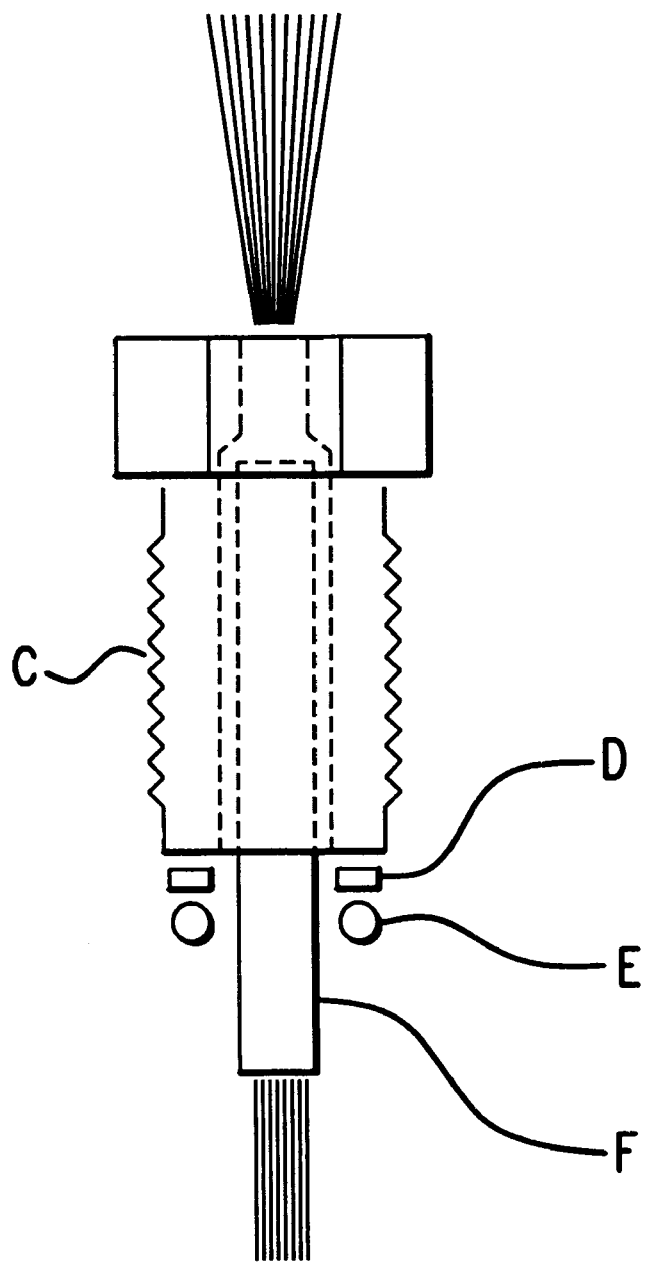
FIG. 3 is a schematic diagram of the injection manifold for the MCAE system.
Figure 4A:
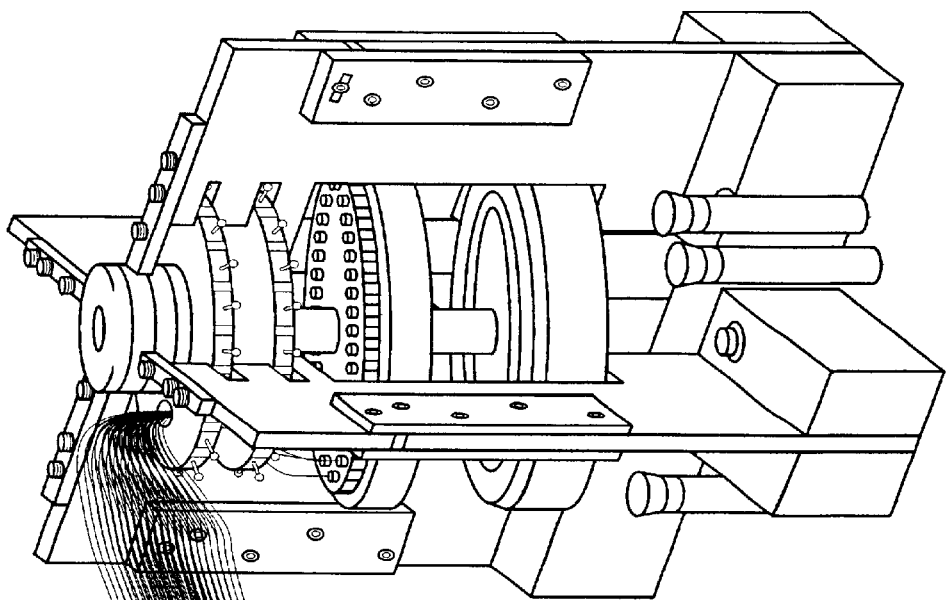
FIGS. 4A and 4B show the loading system presently being used and a capillary bundle ready for injection.
Figure 4A:
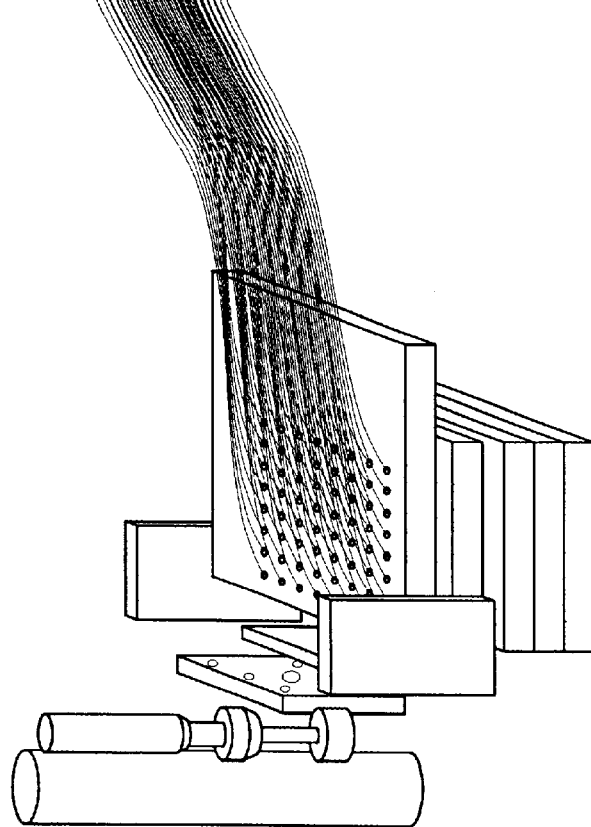
Figure 4B:
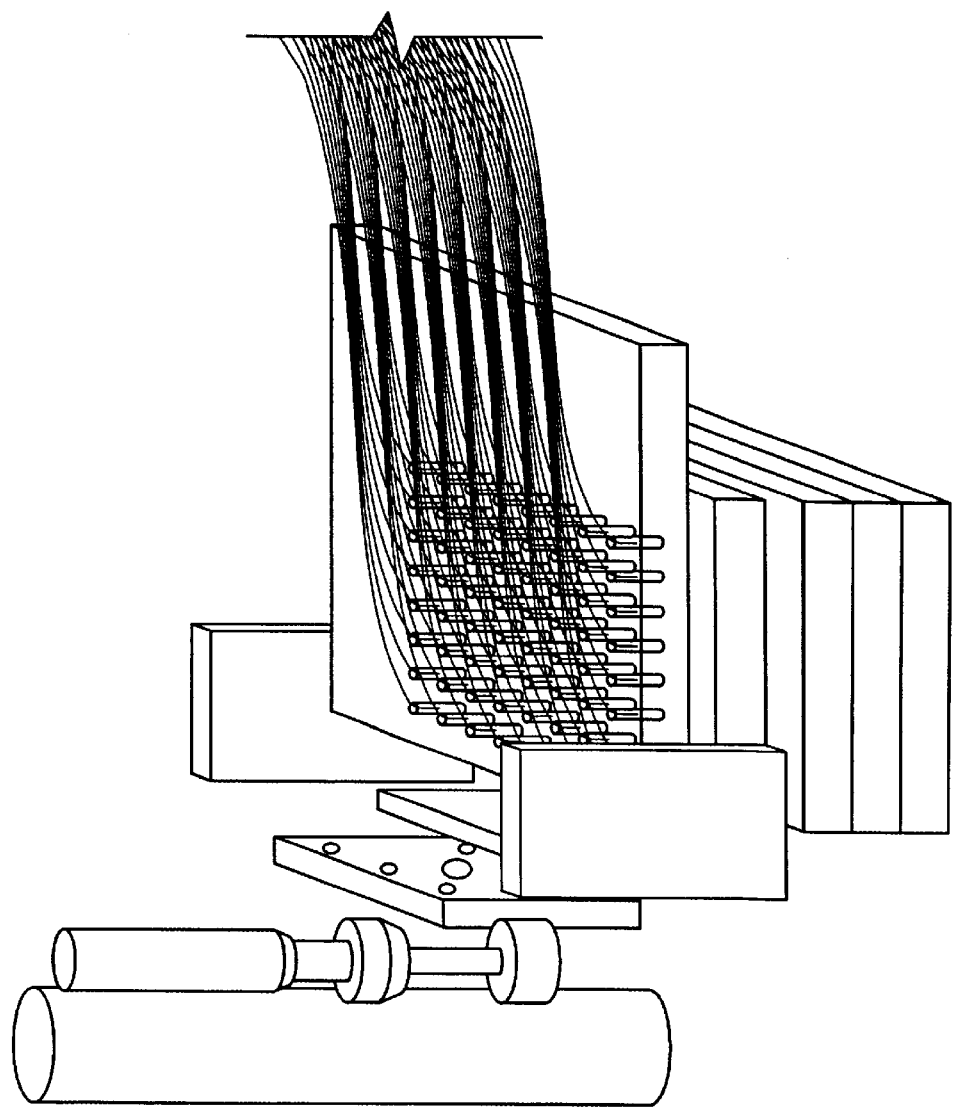

Eight groups of 32 capillaries from one quadrant are led to a common area where up to 256 capillaries can be loaded with sample using electrokinetic injection. Each quadrant has its own loading area which allows us to inject up to a total of 1024 samples. We have designed an injection geometry employing a stainless steel sample injection plate that allows us to reproducibly control the extent of injection. A schematic diagram of the injection assembly is shown in FIG. 3 (center). Sample is loaded into the wells of the injection plate. The sample wells are interleaved with holes with corresponding spacing. The cathode end of the capillaries are threaded into guide holes in a Lucite plate (FIG. 3 top) and a restraining plate is lowered on the capillaries causing them to bend above the point of entry. The injection plate is positioned so the capillary tips are centered on the centers of the injection wells. The capillary plate is lowered with micrometer control until each of the capillaries has made contact with the bottom of their respective sample wells. The array is now self leveled. The group of capillaries is now raised by an amount which is about half the depth of the sample (~600 $\mu$m) and injection voltage is applied. After loading, the capillaries are raised above the well plate, the well plate is translated to the hole position and the capillaries are lowered into the running buffer which is positioned immediately below the well plate. FIG. 4A shows a bundle of capillaries loaded into the injector. FIG. 4B shows the tips of the capillaries above the injection plate after being self leveled. The capillaries have been illuminated from the side to make the tip sections visible.

Figure 1:
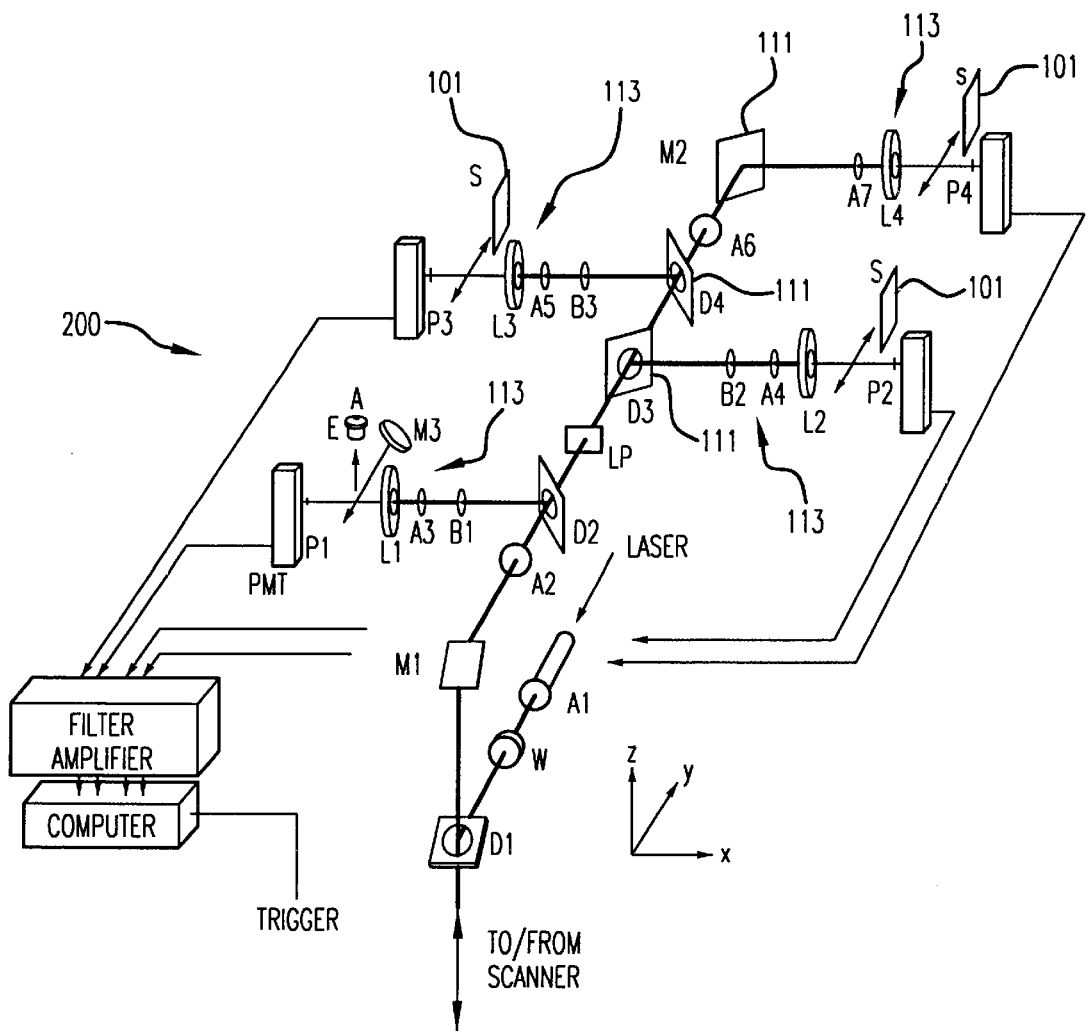
FIG. 1 is a schematic diagram of the four-color confocal fluorescence detection system.

FIG. 1 shows our four-color detection module that is currently being used for sequencing. The laser beam is deflected downward by the dichroic beam splitter, D1, and into the top of the scanner shown in FIGS. 2A–C. In order to make the intensity and polarization of the laser beam at the capillaries independent of rotor position, a quarter wave plate (488 nM) is inserted between the laser and aperture A1. This also insures that polarized light, such as Raman scattering, is reflected equally by the dichroic beam splitters following D1 and is independent of rotor position.

The HC 120-07 photomultipliers used in this four-color detection unit have bandwidths of 200 kHz (Hammamatsu, Bridgewater, N.J.). The rotating laser beam initiates data acquisition by means of a trigger signal from a pinhole apertured photodiode placed ahead of the first capillary to be measured and within the diverging beam of the objective. The trigger initiates simultaneous data collection from four independent ADCs on a 3400a data acquisition board (Microstar Laboratories, Bellview, Wash.) with sample times of 11.55 microsecond per data point. The rotation speed of the rotor (set to 4.008337 rev/sec) exactly matches the data rate to give exactly 18 data points across the repeat spacing of the capillaries. The precision of the rotation is such that the last capillary to be measured in one rotation is in exact registration with its expected data position. The ADC board contains it's own 486 microprocessor and performs data stripping and averaging both across the capillaries and for successive cycles in real time. A rotation speed of four revolutions/sec was chosen to hit all DNA fragments passing the detection zone of the capillary which, because of the cylindrical capillary geometry, is about 30 microns long.

As discussed above, to demonstrate the positional accuracy of the scanner, we have arranged groups of 8 capillaries at the beginning of each of the four quadrants of the scanner and one capillary at the end of the last quadrant. A 1 nM fluorescein solution in 1×TBE was circulated through all 33 capillaries and the fluorescence signals detected from one rotation of the scanner (21500 data points) is shown in FIG. 5a. The laser power was 240 mW at the sample. The blue, green, black and red traces are the signals from channels 1–4 (520 nm, 550 nm, 580 nm, >600 nm). FIG. 5b shows the group of 8 capillaries in the third quadrant. FIG. 5c presents the results of a sequencing run of M13 in one capillary under scanning conditions. This run had a S/N that is as good or better than the conventional flat bed capillary array scanners that we are using for sequencing. We have demonstrated that the processor can obtain similar data on up to 1088 capillaries at once.

Finally, the image in FIG. 6 presents the results of 128 capillary sequencing runs detected with the MCAE scanner. This image shows that high quality sequencing runs can be readily obtained on large numbers of capillaries in parallel. Each of these separations can be called to over 500 bases.

On this basis, the instant invention should be recognized as constituting progress in science and the useful arts, as solving the problems in the large-scale genomic sequencing studies enumerated above.

Having described preferred embodiments of the invention, it is to be understood that the invention is not limited to those precise embodiments, and that the various changes and modifications may be effected therein by one skilled in the art without departing from the scope or spirit of the invention as defined in the appended claims. Thus, the scope of the invention should be determined by the appended claims and their legal equivalents, rather than by the examples given.

What is claimed is:

1. A capillary array electrophoresis apparatus comprising:
   two cylinders, each having a side;
   a plurality of capillary tubes disposed in a circular array on the sides of the two cylinders;
   a source of radiant energy of a first wavelength;
   a rotor means for rotating in a single direction;
   an objective lens, mounted on the rotor means, for receiving and focusing the radiant energy of a first wavelength onto the capillary tubes;
   a dichroic beam splitter mounted on the rotor means;
   confocal spatial and spectral filter means for transmitting radiant energy of a second wavelength emitted from the capillaries and rejecting radiant energy of other wavelengths; and,
   a detector means for measuring the intensity of the second radiant energy.

2. The capillary array electrophoresis apparatus of claim 1, further comprising:
   computer means for process control, data processing, and for controlling the rotor means.

3. The capillary array electrophoresis apparatus of claim 1, wherein the rotor means is connected to a micro-stepping indexed motor.

4. The capillary array electrophoresis apparatus of claim 1, wherein said detector means is a four-color detection means incorporating photomultiplier means.

5. The capillary array electrophoresis apparatus of claim 1, wherein the radiant energy of a first wavelength is passed through a quarter-wave plate calibrated at about 488 nM.

6. The capillary array electrophoresis apparatus of claim 1, further comprising a photodiode positioned between the objective lens and a capillary, wherein the radiant energy of a first wavelength initiates data acquisition by illuminating the photodiode.

7. The capillary array electrophoresis apparatus of claim 1, wherein said tubes are mounted in grooves on a side of said cylinders.

8. The capillary array electrophoresis apparatus of claim 1, wherein said tubes are substantially adjacent to one another.

9. The capillary array electrophoresis apparatus of claim 1, incorporating at least about 1024 of said tubes.

10. The capillary array electrophoresis apparatus of claim 1, wherein the source of radiant energy of a first wavelength is a coherent light source.

11. The capillary array electrophoresis apparatus of claim 10, wherein the coherent light source is a laser.

12. The capillary array electrophoresis apparatus of claim 1, wherein the detector means is a two-dimensional image array detector.

13. The capillary array electrophoresis apparatus of claim 12, wherein the array detector is selected from a group consisting of a charge-coupled device and a charge-injection device.

14. The capillary array electrophoresis apparatus of claim 1, wherein the cylinders are connected to one another by at least three posts.

15. An apparatus for determining the sequence of a nucleic acid sample, the apparatus comprising:
   two cylinders, each having a circumference;
   a plurality of electrophoresis lanes disposed along the circumference of the cylinders in a circular array;
   a source of radiant energy of a first wavelength;
   an optical detection system for detecting radiant energy of a second wavelength emanating from the electrophoresis lanes, the optical detection system comprising:
   (i) collection optics for collecting and focusing the radiant energy of a second wavelength;
   (ii) a detector for measuring the intensity of the radiant energy of a second wavelength; and,
   (iii) a rotary scanner for directing the radiant energy of a first wavelength to each electrophoresis lane.

16. The apparatus of claim 15, wherein the rotor means is connected to a micro-stepping indexed motor.

17. The apparatus of claim 15, wherein the detector means is a four-color detection means incorporating photomultiplier means.

18. The apparatus of claim 15 wherein the source of radiant energy of a first wavelength is a coherent light source.

19. A capillary array electrophoresis apparatus, the apparatus comprising:

a source of radiant energy of a first wavelength;

at least one cylinder having a circumference;

a rotor;

an objective lens, mounted on the rotor and housed within the at least one cylinder, for focusing the radiant energy of a first wavelength, wherein the objective lens is positioned in the path of the radiant energy;

a plurality of capillaries positioned along the circumference of the at least one cylinder and in the path of the radiant energy of a first wavelength focused by the objective lens; and at least one detector for detecting radiant energy of a second wavelength emitted from the capillaries.

20. The capillary array electrophoresis apparatus of claim 19, further comprising a photodiode positioned between the objective lens and a capillary such that illumination of the photodiode initiates detection by the detector.

21. A capillary array electrophoresis apparatus, the apparatus comprising:

a source of radiant energy of a first wavelength;

three vertical posts;

two cylinders, each having a circumference, wherein the two cylinders share a common vertical axis and are mounted on the posts;

a rotor;

an objective lens, mounted on the rotor and housed within the at least one cylinder, for focusing the radiant energy of a first wavelength, wherein the objective lens is positioned in the path of the radiant energy;

a plurality of capillaries positioned along the circumference of the at least one cylinder and in the path of the radiant energy of a first wavelength focused by the objective lens;

four dichroic beam splitters, each calibrated to pass a different wavelength of radiant energy emitted from the capillaries and to reject all other wavelengths; and four photodetectors, each of which measures the intensity of radiant energy passed to it by one of the beam splitters.

* * * * *

UNITED STATES PATENT AND TRADEMARK OFFICE
CERTIFICATE OF CORRECTION

PATENT NO.    : 6,270,644 B1                                    Page 1 of 3
DATED         : August 7, 2001
INVENTOR(S)   : Mathies et al.

It is certified that error appears in the above-identified patent and that said Letters Patent is hereby corrected as shown below:

Column 7,
Lines 64 and 67, please delete the text.

Fig. 2B should appear as follows:

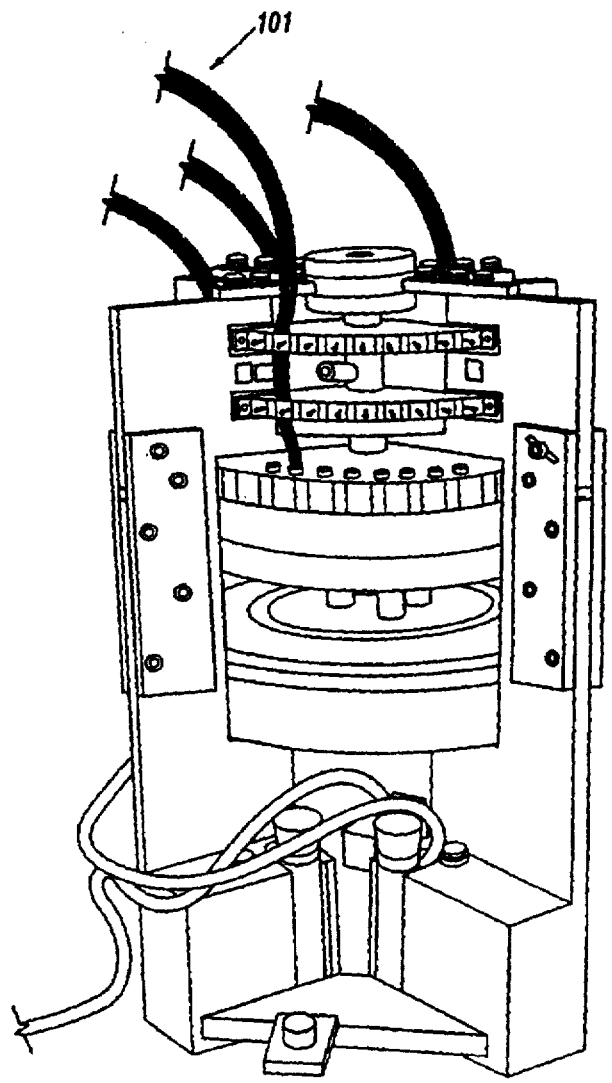

UNITED STATES PATENT AND TRADEMARK OFFICE
CERTIFICATE OF CORRECTION

PATENT NO. : 6,270,644 B1
DATED : August 7, 2001
INVENTOR(S) : Mathies et al.

It is certified that error appears in the above-identified patent and that said Letters Patent is hereby corrected as shown below:

Figure 2C should appear as follows:

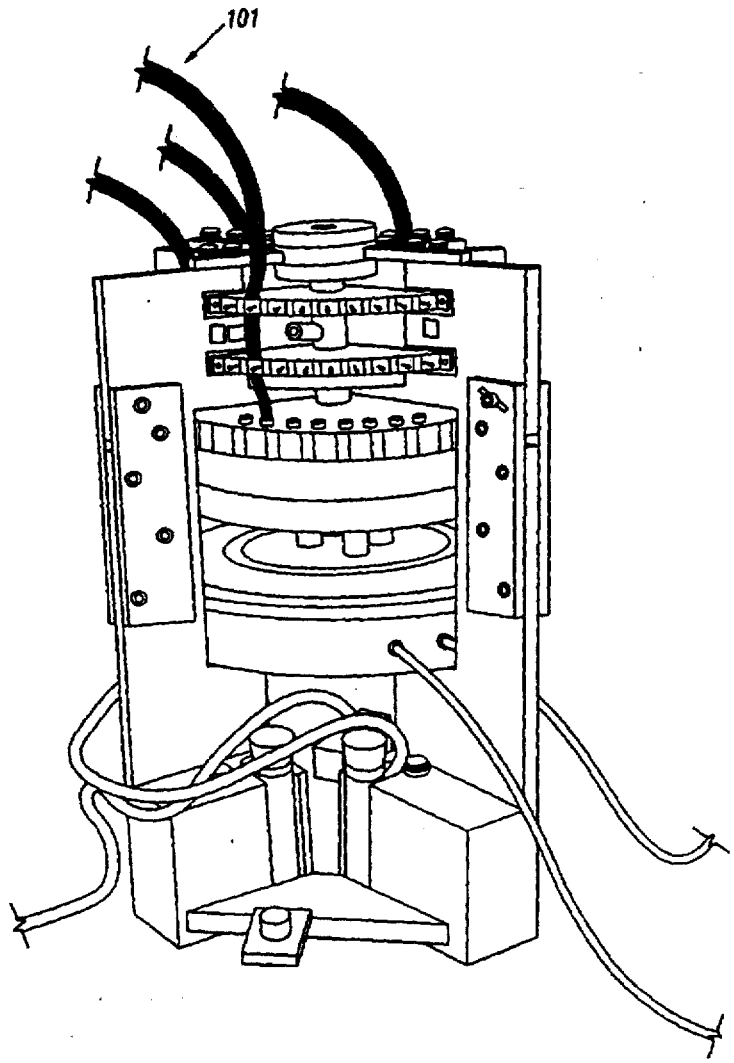

UNITED STATES PATENT AND TRADEMARK OFFICE
CERTIFICATE OF CORRECTION

PATENT NO. : 6,270,644 B1
DATED : August 7, 2001
INVENTOR(S) : Mathies et al.

It is certified that error appears in the above-identified patent and that said Letters Patent is hereby corrected as shown below:

Figure 4A should appear as follows:

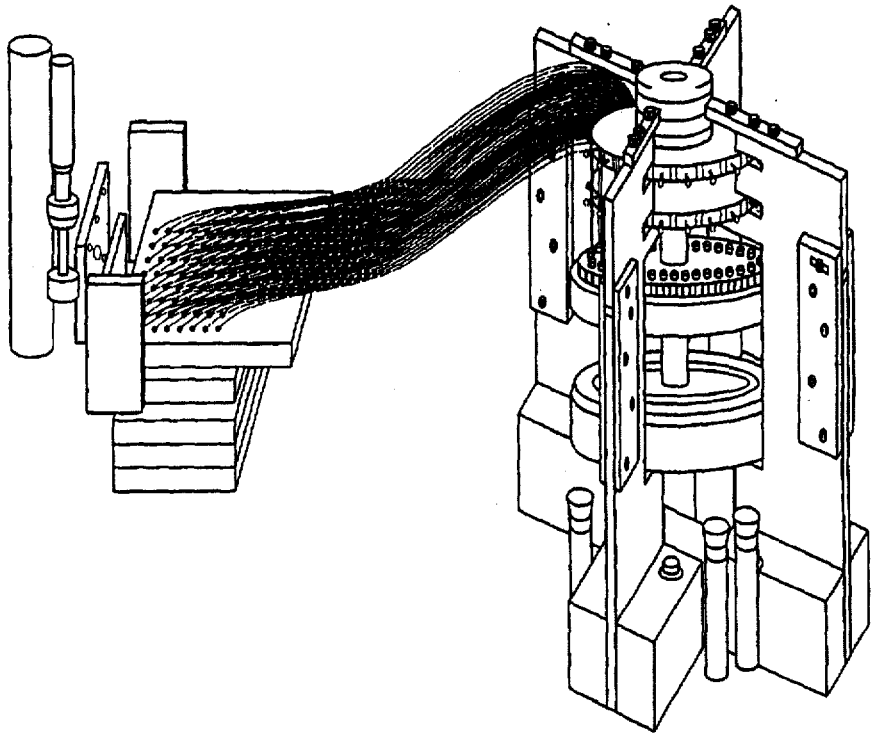

Signed and Sealed this

Fifth Day of February, 2002

*Attest:*

JAMES E. ROGAN
*Attesting Officer*   *Director of the United States Patent and Trademark Office*